United States Patent
Dabi et al.

[11] Patent Number: 5,916,507
[45] Date of Patent: Jun. 29, 1999

[54] METHOD OF FORMING A UNITIZED ABSORBENT PRODUCT WITH A DENSITY GRADIENT

[75] Inventors: Shmuel Dabi, Highland Park; Kays Chinai, Burlington, both of N.J.

[73] Assignee: McNeil-PPc, Inc., Skillman, N.J.

[21] Appl. No.: 08/335,220

[22] Filed: Nov. 7, 1994

Related U.S. Application Data

[63] Continuation of application No. 08/158,836, Nov. 24, 1993, abandoned, which is a continuation of application No. 07/714,122, Jun. 11, 1991, abandoned.

[51] Int. Cl.$^6$ .............................. B32B 31/20; D04H 1/42; D04H 1/44; D04H 1/54
[52] U.S. Cl. ...................... 264/113; 156/62.2; 156/62.8; 264/119; 264/122; 264/126
[58] Field of Search .................... 156/62.2, 62.8, 156/181, 296, 312; 264/113, 119, 120, 126, 122; 604/366, 368, 369, 370, 379

[56] References Cited

U.S. PATENT DOCUMENTS

| | | | |
|---|---|---|---|
| Re. 26,151 | 1/1967 | Duncan et al. | 128/284 |
| 2,788,003 | 4/1957 | Morin | 128/284 |
| 3,017,304 | 1/1962 | Burgeni | 156/281 |
| 3,768,480 | 10/1973 | Mesek et al. | 128/287 |
| 3,771,525 | 11/1973 | Chapuis | 128/290 R |
| 4,134,948 | 1/1979 | Baker, Jr. | 264/518 |
| 4,259,958 | 4/1981 | Goodbar | 128/287 |
| 4,449,979 | 5/1984 | Holtman | 604/379 |
| 4,540,454 | 9/1985 | Pieniak et al. | 156/62.2 |
| 4,554,297 | 11/1985 | Dabi | 521/178 |
| 4,795,335 | 1/1989 | Farrington et al. | 425/82.1 |
| 4,818,315 | 4/1989 | Hellgren et al. | 156/296 |
| 4,900,377 | 2/1990 | Redford et al. | 156/62.2 |
| 4,988,345 | 1/1991 | Reising | 604/368 |
| 5,039,431 | 8/1991 | Johnson et al. | 156/62.8 |
| 5,079,074 | 1/1992 | Steagall et al. | 428/296 |
| 5,171,391 | 12/1992 | Chmielewski et al. | 604/379 |

FOREIGN PATENT DOCUMENTS

| | | | |
|---|---|---|---|
| 70164 | 1/1983 | European Pat. Off. | 156/62.8 |
| 165807 | 12/1985 | European Pat. Off. | |

OTHER PUBLICATIONS

A.A. Burgeni and C. Kapur, "Capillary Sorption Equilibria in Fiber Masses," Reprinted from Textile Research Journal, vol. 37, No. 5, May, 1967.

*Primary Examiner*—Steven D. Maki
*Attorney, Agent, or Firm*—Joel A. Rothfus

[57] ABSTRACT

A method of constructing multi-layer products for absorbing fluids is disclosed. In the methods of the present invention, two or more layers of materials chosen to vary in recovery are compressed such that an absorption gradient forms through the continuous intimately associated layers. A first layer preferably remains densified while a second layer "blooms" to form an open, absorptive layer, which acts as a reservoir, drawing absorbed fluids into the densified layer, where they are retained.

13 Claims, 1 Drawing Sheet

METHOD OF FORMING A UNITIZED ABSORBENT PRODUCT WITH A DENSITY GRADIENT

This is a continuation of application Ser. No. 08/158,836 filed on Nov. 24, 1993, now abandoned which is a continuation of Ser. No. 07/714,122, filed on Jun. 11, 1991, now abandoned.

FIELD OF THE INVENTION

The present invention relates to absorbent products. More particularly, the present invention relates to a method of forming a unitized absorbent product with a density gradient.

BACKGROUND OF THE INVENTION

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially, in many of these products, especially diapers and sanitary napkins, the absorbent batt comprised what is termed "wadding" or plies of tissue. The wadding was disposed between an impermeable backing and a permeable facing and the plies of tissue were used to absorb and, hopefully contain the liquid within the product. A diaper which utilizes such an absorbent batt is disclosed in U.S. Reissue Pat. No. 26, 151.

The wadding type of batt was replaced, for the most part, by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also the fluffed wood pulp layer is quite soft, flexible and conformable and hence, produces an improved diaper over diapers using wadding as the absorbent layer.

Though the fluffed wood pulp absorbent batts have improved capacity, the total absorbent capacity of the batts is often not entirely used, causing leakage and/or staining. Because fluid to be absorbed is generally deposited in a localized area within the absorbent batt and radiates equally in all directions, the fluid tends to reach the longitudinal sides of a generally-rectangular batt before it reaches the ends of the batt. Consequently, the absorbent product may leak at the longitudinal sides.

The ability of a densified pulp to transport fluid more effectively than traditional products made from a uniform wood pulp fluff has been recognized. A. Burgeni and C. Kapur, "Capillary Sorption Equilibria in Fiber Masses," Test Res. J., Vol. 37:5, p.356, (1976).

A multi-layer diaper is disclosed in Mesek et al. U.S. Pat. No. 3,768,480. Mesek et al. describes a batt having a density gradient achieved by gradually decreasing the proportion of long fibers and increasing the level of short fibers in a blend. Typically, this structure is then bonded with a latex binder and serves as a facing layer in conjunction with a second batt layer and a water impervious backing sheet.

U.S. Pat. No. 3,771,525 discloses a traditional layered structure. A high density cotton core is wrapped with a low density, loose cotton fiber layer.

A method of making a selectively densified fiber batt obtained from an embossed pattern made permanent by employing an adhesive is described in U.S. Pat. No. 4,134,948. This method makes an absorbent fabric comprising a batt of randomly arranged, intermingled cellulosic fibers having a plurality of high loft, loosely compacted regions separated from each other by highly compressed regions. These compressed regions are formed by moistening the batt, embossing the batt for providing a pattern in the surface, and applying an adhesive material to the patterned surface. The adhesive penetrates through the compressed regions to form banded fiber networks and only partially penetrates through the high loft absorbent regions.

In U.S. Pat. No. 4,540,454, a method of forming a relatively thin absorbent product is disclosed. The product has at least two layers. One layer may be superimposed on the other by air layering. The layers are then compressed at a pressure adequate to collapse the entire structure which promotes intimate contact between the layers; a wicking layer and an absorbing layer. The structure in its compressed form is less than one-half its thickness in the uncompressed form. The absorbing layer is a low density, resilient, fibrous web consisting of randomly disposed, frictionally entangled fibers which result in a web having a dry bulk recovery of at least 60 percent, an initial dry bulk of at least 20 cc/gm and a weight less than about 2 oz/yd$^2$. The fibrous web making up the absorbing layer is used to specially distribute superabsorbent material so that upon exposure to an aqueous, swelling occurs with minimal interference from adjacent superabsorbing material. The transporting or wicking layer is a high density structure made of particles such as cellulosic fibers, peat moss, or mixtures thereof.

SUMMARY OF THE INVENTION

Despite the numerous constructions disclosed in the prior art, today's absorbent disposable products, such as diapers and sanitary napkins, face an increased demand for better performance. Absorbent products are expected to absorb body fluids, contain them well without leakage, and minimize skin wetness which can cause irritation. Consequently, the products described in the prior art generally have multiple layers which are combined to form one structure with a capillary gradient. The multi-layer approach has at least two drawbacks: (1) the lack of intimate contact between layers may inhibit fluid flow, and any separation during the use of the product is detrimental to that purpose; and (2) a slow and costly multistep process is required to prepare and combine the layers.

It is, therefore, an object of this invention to prepare an absorbent structure for the efficient transport of fluids away from the skin. The absorbent structures of the products of this invention contain a variety of materials differing in resilience which are in substantially continuous contact such that they form a density gradient. The density gradient may be formed by exposing deposited materials to compressive forces and then removing the forces, forming a density gradient due to the differences in recovery of the layers. The present invention provides methods of forming such an absorbent structure by, e.g., depositing a first layer of compressible absorbent material, such as wood pulp, and depositing at least one subsequent layer of a resilient material, such as a blend of synthetic resilient fibers and wood pulp, on top of at least a portion of the first layer and applying pressure to at least a portion of the first and subsequent layers sufficient to cause the first compressible layer to remain substantially compressed after the pressure is released.

Also provided by this invention are the absorbent multi-layered structures produced by the methods of this invention.

DETAILED DESCRIPTION OF THE INVENTION

Figure 1:
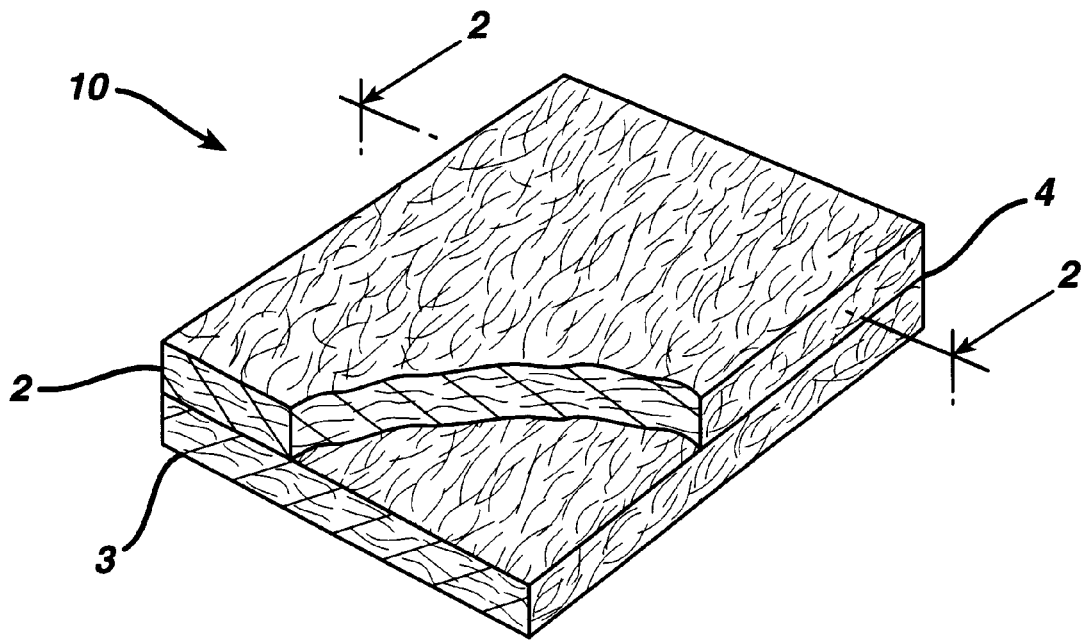
FIG. 1 is a perspective view, partially broken away, of a multi-layered absorbent structure made in accordance with the present invention.

The method of this invention provides for the formation of two or more layers of material into an absorbent structure, which upon compression, forms an absorption gradient to transport fluid effectively away from contact with skin. Referring now to the drawings and by way of example, FIG. 1 represents a perspective view of a two-layered structure 10. In the methods of the present invention, the first layer 3 results from depositing a compressible absorbent material. At least one subsequent layer 2 is superimposed on the first layer 3 by depositing a material that is relatively more resilient upon removal of compressive forces than the material of the first layer. A transition 4 between the layers is visible depicting the lack of intimate contact between layers 2 and 3. The density zones or absorbent gradient ultimately produced, result from compression of this multi-layered structure 10 and the difference in compressibility between the layers 2 and 3.

Figure 2:
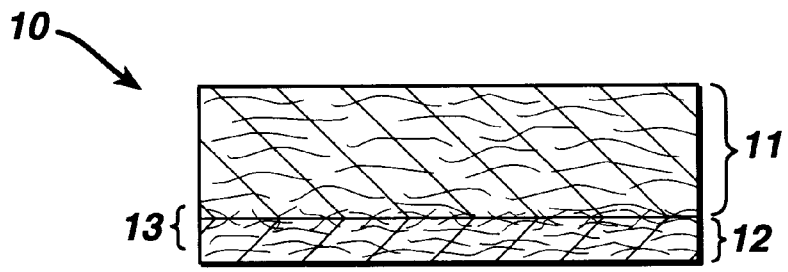
FIG. 2 is a cross-sectional view of an absorbent product made in accordance with the present invention and taken along line 2—2 in FIG. 1.

Referring now to FIG. 2, a cross-sectional view of an absorbent product 10 is produced by the method of this invention is depicted. After the structure depicted in FIG. 1 is compressed, the subsequent layer 2 does not remain densified upon removal of the compressive force, but instead recovers to form an open top layer 11 which does not collapse when wet. A "reservoir" effect is thus provided by the lower density open top layer 11 as it draws fluid toward the higher density absorbent first layer 12 which remains substantially compressed. The transition area 13 illustrates how the compressed layer 12 is in intimate and continuous contact with the open layer 11. The method of the present invention thus provides critical continuity between layers 11 and 12, and ensures efficient fluid transfer by the formation of a density gradient, low to high, without the interruption of adhesives. The structure depicted thus provides a soft and relatively dry layer that is generally intended for bodily contact.

The first layer 3 to be deposited is therefore preferably comprised of compressible absorbent material. As used herein, "compressible absorbent material" refers to any absorbent material, that upon removal of compressive forces, remains substantially compressed. Examples of suitable compressible absorbent materials are known to those skilled in the art and include cellulosic fibers such as wood pulp and rayon. Other compressible absorbent materials are known to those of skill in the art.

Preferably, superabsorbent particles are dispersed in the first layer 3. Superabsorbent materials are known to those skilled in the art and are more fully described, for example, in U.S. Pat. No. 4,540,454 which patent is hereby incorporated by reference. Generally, a superabsorbent material is a water-insoluble, water-swellable polymer material capable of absorbing water in an amount which is at least ten times the weight of the substance in its dry form.

At least one subsequent layer 2 of material that is relatively more resilient upon removal of compressive forces than the material of the first layer 3 is deposited on top of at least a portion of the first layer 3. The materials of this layer tend to recover to substantially the same thickness and/or density after exposure to compressive forces. This property is described within the context of this invention to be "resiliency". By depositing at least one resilient material layer 2 and compressing the thusly formed multi-layered structure 10, a density gradient is obtained due to differences in recovery of the layers after the compressive forces are released.

Where an absorbent structure of more than two layers is desired, it is preferred that each subsequent layer be comprised of material that is relatively more resilient upon removal of compressive forces than the material of the previous layer, thereby providing a product that recovers from the top lower density layer towards the first higher density layer, thus yielding a density gradient. The term "blooms" as used herein refers to recovery of the layers after removal of compressive forces wherein the top layer recovers to a greater percentage of its original uncompressed state than the next adjacent layer and so on until the first layer, which remains substantially compressed. The term "resilient material" as used herein refers to a material that is capable of recovering to at least 25% of its original thickness after exposure to the quantity of pressure which is sufficient to cause the first high density layer 3 to remain substantially compressed after such pressure is released. The resilient material of this invention includes fibers which may be characterized as "hydrophobic", or relatively moisture-insensitive. Such material generally does not absorb fluid to any substantial degree or swell in the presence of body fluids and, generally exhibits less than 5% weight gain in water as measured on an individual fiber, i.e., the net gain from imbibed water as opposed to interstitial water.

The dry resilience of the material of the subsequent layer 2 permits the compressed structure 10 to recover substantially immediately after removal of compressive forces, and to form an "open" layer 11 which does not collapse in the wet state, such as in use and thus remains soft. Suitable materials are generally synthetic fibers of hydrophobic polymers or absorbent fibers that are treated to be hydrophobic. Preferably, said fibers have a denier of between about 1.5 and about 15. For example, fibers of polyester, polyamide (nylon), polypropylene, acrylic, polyvinylchloride and its vinyl acetate copolymers, polyurethane and elastic fibers made from polyolefins or styrene block copolymers and the like are suitable for use in the products of this invention. In addition, bicomponent fibers constructed of such materials are also suitable for use in the products of this invention. Also suitable are particles of resilient ground foam such as polyurethane, polyester foam and poly (amino ether) foam of the type described in U.S. Pat. No. 4,554,297. Blends of any of the above are also contemplated for use in the method of this invention. There should be between about 5 and about 100% by weight of resilient fibers present in the resilient layer. Preferably, there should be between about 10 and about 80% by weight; most preferably between about 15 and about 50% by weight.

Depending on the desired density gradient formed by the layers in the final absorbent product, up to 95% by weight of the resilient material in the subsequent layer 2 can be made up of any hydrophilic material such as wood pulp fluff, rayon or cotton, provided that the layer 2 remains capable of recovering to at least 25% of its original thickness as detailed herein. In an preferred embodiment, subsequent layers of polyester fiber could be deposited over the first absorbent layer 3 with each subsequent layer having decreasing amounts of wood pulp contained therein.

The resilient material may additionally include a surfactant to avoid excessive water repellency and to promote the movement of fluids through the gradient and away from the body. A polyoxyethylene sorbitan monolaureate sold by ICI of Wilmington, Del. under the tradename TWEEN 20 is expected to be useful as are other nonionic and anionic wetting agents known to those skilled in the art.

The use of thermoplastic binder fibers in any of the various layers is also within the method of this invention. Depending upon the binder chosen, e.g., a binder fiber of a polyester core with polyethylene sheath included in the lower density subsequent layer, care should be taken to carry out the compression at a sufficiently low temperature to avoid permanent densification of a resilient subsequent layer due to melting of the binder fibers. However, in the first layer 3, pressure and heat can be utilized advantageously with binder fibers to achieve greater density if desired.

Once the layers 2 and 3 have been deposited, the relatively loose multi-layer structure 10 should be compressed at a pressure and for a time and temperature sufficient to cause the first layer 3 to remain substantially compressed after the pressure is released. The compression can be carried out in the presence of moisture and at different temperatures to vary the resultant density gradient such as would be suitable for the ultimate product. Higher moisture levels and higher temperature result in greater density within the layers. Once compressed, the unitized absorbent product of this invention, with intimate and continuous contact between layers and having a density gradient, arises. The layers 11 and 12 overlap and diffuse into each other upon compression so that no sharp boundaries can be defined in contrast to a transition zone 4 which is clearly visible prior to compression. The use of adhesives or other means to secure contact between adjacent layers in an absorbent product is obviated by the method of the present invention.

The amounts of pressure to which the structures of this invention should be subjected vary with respect to the materials being used. For example, in a structure containing a high density layer of 100% pulp and a resilient layer containing about 15% polyester fibers and 85% pulp, a pressure of between about 1,000 and about 10,000 psi should be imposed on the structure for a period of time of between about ½ sec. and 5 secs. The compression may take place at ambient temperature, or may be conducted at an elevated temperature, preferably between about 25 and 150° C. Subjecting the structure to pressure at higher temperatures will generally create a denser high density layer if that layer is made of pulp.

Additionally, after recovery to at least 25% of the original thickness of a resilient subsequent layer 11 upon removal of compressive forces, the product 10 and its thusly formed density gradient can be stabilized by heating the product. Such stabilization results in a product that is less susceptible to compression during use and therefore tends to remain softer to the touch.

The deposition of the various layers can be accomplished by a variety of techniques known to those skilled in the art, such as air layering and water casting. A particularly suitable technique is described in U.S. Pat. No. 4,795,335 which is hereby incorporated by reference, describes the use of a multi-headed ductless webber to make absorbent batts. Generally, a lickerin and feed mechanism create a supply of particulate or fibrous material. The materials are deflected from the lickerin in the form of an entrained stream of material by means of a plate. A conveying screen intercepts the entrained material and accumulates it into a web. Multiple lickerins and feed mechanisms may be spaced along the conveying screen for multi-layered products.

The method of the present invention produces a unitized absorbent product suitable for use in a variety of absorbing products. Examples include, but are not limited to, the use of the absorbent product produced by the process of this invention in products destined for absorbing bodily fluids, e.g., sanitary napkins, diapers, wound dressings and drapes.

Preferred embodiments of the invention are described in the following non-limiting examples:

EXAMPLE 1

A blend of 15% Dacron Hollofil brand polyester fiber available from E. I. duPont de Nemours located in Wilmington, Del. (5.5 denier, 1.5" long) and 85% wood pulp made of bleached Kraft material available from International Paper Company was air-laid onto a pure wood pulp fluff layer of equal basis weight using a multi-headed ductless webber. This was accomplished using a Fitzmill equipped with a vacuum forming section. The resulting low density pad was then compressed for 30 seconds at room temperature (25° C.) under 5,000 psi. The pressure was then removed. A slow recovery of the top layer (to at least 25% of its original thickness) began, leading to a visible density gradient within 2 minutes. Ten milliters of synthetic menstrual test fluid having a viscosity of 270 cps (centipoise), and a pH of 7 was deposited at once on the low density subsequent layer. The fluid was accepted instantaneously by that layer and then almost completely transferred into the bottom high density layer 12, leaving a surface dry to the touch.

The same method of layering was used as described in Example 1 except that the bottom layer contained wood pulp, IM-1000 brand superabsorbent available from Hoechst-Celanese in a ratio of 90/10 and the top layer was 85/15 (by weight) (blend of pulp and bicomponent polyester fiber (D-270,4 denier, sold by E.I. duPont de Nemours & Co., Wilmington, Del.). The low density web was compressed at room temperature as in Example 1 and then allowed to "bloom". After a recovery to 50% of the original thickness of the top layer was attained, the composite structure was stabilized by heating for 2 minutes at 145° C. A permanently stabilized low density zone which is less susceptible to compression in use was obtained.

We claim:

1. A method of forming an absorbent structure comprising:
   (a) forming a first layer comprised of compressible absorbent material having superabsorbent material dispersed therein;
   (b) depositing a second layer having an original thickness that is comprised of a blend of at least two materials on top of at least a portion of said first layer, said blend of at least two materials including hydrophilic material and at least 5 wt-% of a resilient material selected from the group consisting of synthetic fibers and foams, the resilient material being relatively moisture-insensitive and selected to withstand collapse in a wet condition and to provide said second layer with a predetermined degree of resiliency;
   (c) applying pressure to at least a portion of said first and second layers so as to compress said first and second layers into a unitized structure, said pressure being maintained for a time and at a temperature sufficient to (i) cause said first layer to remain substantially compressed after the pressure is released, and (ii) allow said second layer to expand to at least 25% of its original thickness after said pressure is released; and (d) expanding the second layer by releasing the pressure so the second layer expands so as to recover at least 25% of its original thickness, while the first layer remains substantially compressed and has a greater density than the second layer, wherein the first and second layers are in intimate contact at their interface without the interruption of an adhesive.

2. The method of claim 1 wherein the compressible absorbent material comprises cellulosic fiber or a mixture of cellulosic fibers.

3. The method of claim, 1 wherein said hydrophilic material comprises wood pulp, said wood pulp forming not more than 95% by weight of said blend.

4. The method of claim 1 wherein the layers are of equal basis weight.

5. The method of claim 1 wherein at least one of said first and second layers further comprises thermoplastic binder fibers.

6. The method of claim 1 further comprising the step of heating at least a portion of said first and second layers following the step of expanding the second layer to stabilize the thickness of the first and second layers.

7. The method according to claim 1 wherein thermoplastic binder fibers are disposed in said first layer, and the step of applying pressure to said layers further comprises applying heat to said first layer so as to cause said binder fibers to melt, thereby maintaining increased density of said first layer after said pressure is released.

8. The method of forming an absorbent structure comprising:

(a) forming a first layer comprised of compressible absorbent material;

(b) depositing a first subsequent layer comprised of a resilient material on top of at least a portion of said first layer;

(c) depositing a second subsequent layer comprised of a resilient material on top of at least a portion of said first subsequent layer;

(d) applying pressure to at least a portion of said first layer and subsequent layers for a time and at a temperature sufficient to compress said first layer and subsequent layers and to cause said first layer to remain compressed after the pressure is released; and (e) expanding the subsequent layers by releasing the pressure, wherein the first layer remains compressed while said first subsequent layer and second subsequent layer expand and the second subsequent layer recovers a greater percentage of its original thickness than the first subsequent layer, wherein the first layer and subsequent layers are in intimate contact at their interfaces.

9. The method of claim 8 wherein the compressible absorbent material comprises cellulosic fiber or a mixture of cellulosic fibers.

10. The method of claim 8 wherein the compressible absorbent material further comprises a superabsorbent material interspersed therein.

11. The method of claim 8 wherein the layers are of equal basis weight.

12. The method of claim 8 wherein at least one of said first and subsequent layers further comprises thermoplastic binder fibers.

13. The method of claim 8 further comprising the step of heating at least a portion of said first and subsequent layers following the step of expanding the first and subsequent layers to stabilized the thickness of the first and subsequent layers.

* * * * *